United States Patent [19]

Williams

[11] Plant 4,754

[45] Jul. 28, 1981

[54] MINIATURE ROSE PLANT

[76] Inventor: Ernest D. Williams, 1510 Lebanon Ave., Dallas, Tex. 75208

[21] Appl. No.: 145,771

[22] Filed: May 1, 1980

[51] Int. Cl.[3] ..... A01H 5/00

[52] U.S. Cl. ..... Plt./7

[58] Field of Search ..... Plt./10

*Primary Examiner*—Robert E. Bagwill

[57] ABSTRACT

The subject of the present disclosure is a new and distinct variety of miniature rose plant characterized by the deep red color of the buds and flowers and by the profusion of bloom.

1 Drawing Figure

1

The present invention relates to a new and distinct variety of hardy, dwarf, bush type rose plant of the miniature class; the variety being primarily characterized — as to novelty — by deep red buds and flowers which in general color effect are similar to Little Curt, a miniature variety (not patented).

The variety is further characterized by:

The freedom of bloom, with flowers usually borne one to the stem.

Little or no fragrance.

A plant which is vigorous, of rounded upright shape with glossy, small foliage with pointed leaflets; the buds and flowers being similar in form and size to Little Curt (miniature — not patented).

The plant, which has a normal height of 12–14 inches or more, (more compact or dwarf than Little Curt) can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at my nursery located at Dallas, Tex., under conditions of careful control and observation, as a cross between Starburst (U.S. Plant Pat. No. 2,974), as the seed parent and Over the Rainbow (miniature — U.S. Plant Pat. No. 3,472), as the pollen parent.

Subsequent to origination of the variety I successfully reproduced it, at my nursery located as aforesaid, by cuttings; the reproductions having run true in all respects.

The color photograph illustrates the variety including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; upright; seedling; greenhouse; outdoors; cut flowers; garden decoration; potted plant.

Class: Miniature.

Variety name: Big John.

Flowers borne: Usually one to the stem.

Quantity of bloom: Abundant both outside and in greenhouse.

Bud:

2

*Peduncle.*—Medium length; slender but sturdy; erect; medium green. Hairs — few.

*Before calyx breaks.*—Size — Small. Form medium length; pointed with several foliaceous appendages and several tiny fuzz like hairs on surface of bud; with foliaceous parts extending beyond the tip of the bud equal to one-half or less (sometimes more) of its length. Color — medium green, occasionally tinted with bronze (outdoors).

*As calyx breaks.*—Color — deep red, becoming cream to yellow at base. Opening: opens well in all weather.

Bloom:

*Size when fully open.*—Small, averaging about 35–40 mm (1½").

*Petalage.*—Double — averaging about 35–40 petals or more, arranged regularly plus sometimes several small petaloids.

*Form.*—High centered at first, becoming more open in the center, with petals reflexing loosely outward, with petals folded along edges to give a quilled or pointed effect. Open flowers may show stamens.

Petals: Quite thick; velvety on inside and satiny on outside surface.

*Shape.*—Outside petals, broad lanceolate (nearly round) with rounded tip; intermediate — broad lanceolate with rounded tip; inside — lanceolate with acute tip.

Color: Newly opened flower from a plant grown outdoors (1979 season), Dallas, Tex.:

*Outside petals.*—Outside surface — near Blood Red 820, sometimes with streaks or veining of lighter red progressing toward the base and with small yellowish area at base. Inside surface — near Blood Red 820 with lighter red or yellowish veining (not shown on photo) on lower portion and with small yellow area at base.

*Intermediate petal.*—Outside surface — similar to outside petal. Inside surface — similar to outside petal.

*Inner petal.*—Outside surface — similar to intermediate petal; inside surface — similar to intermediate petal.

*General color effect.*—Newly opened flowers — rich velvety deep red. Three days open — color similar to newly opened flowers but less brilliant. Behavior — opens well in all weather. Color lasts well with little fade. Spent petals drop off.

Flower longevity (May 1979) — plant in pot 6–8 days or longer. Cut flowers at living room temperature 4–5 days or longer.

Reproductive organs:

*Stamens.*—Moderate number, arranged regularly about pistils.

*Filaments.*—Varying length, fairly short.

*Anthers.*—Well formed; orange yellow.

*Pollen.*—Moderate amount.

*Pistils.*—Average number.

*Styles.*—Fairly even; medium to short length; bunched.

*Ovaries.*—All enclosed in calyx.

*Hips.*—Few or none.

*Sepals.*—Permanent; spear shaped; recurved against peduncle.

*Seed.*—Few or none.

Foliage:

*Leaves.*—Compound of five (sometimes three or seven) leaflets; fairly small; leathery; glossy.

*Leaflets.*—Shape: broad, nearly oval; apex acute; base rounded or rounded acute. Margin serrate. Color: medium to bronzy green; new growth — normal (medium) green. Rachis: medium strength; upper side may have a few tiny short prickles or hairs, grooved; underside sparsely thorny with few or no tiny prickles. Stipules: medium long; narrow to medium width; medium length; narrow points which turn out usually at about 45 degrees (or more).

Growth:

*Habit.*—Dwarf; bushy; upright; much branched.

*Growth.*—Free vigorous; internodes short.

*Canes.*—Medium; slender; sturdy.

*Main stems.*—Color: medium green.

*Thorns.*—Average; slender; hook slightly downward; color; brown to tan. Prickles — none. Hairs — none.

*Branches.*—Color: medium green. Thorns: moderate number; medium length; slender; nearly straight inclined downward. Medium oval base. Prickles: none. Hairs: none.

The miniature rose plant and its flowers as herein described may vary in slight detail due to climatic, soil and cultural conditions under which the variety may be grown; the present description being of the variety as grown at Dallas, Tex.

The following is claimed:

1. A new and distinct variety of miniature rose plant of hardy, dwarf, bushy, upright, much branched habit, substantially as illustrated and described, characterized by buds and flowers of a velvety deep red color, being of a shade generally near Blood Red 820, or similar, the bud and flower resembling the variety Little Curt (miniature — not patented) in form and size; and further characterized by a plant of vigorous and compact upright growth habit, easy to propagate from cuttings or by budding, with an abundance of small to medium size glossy foliage and an abundance of flowers borne usually one to the stem.

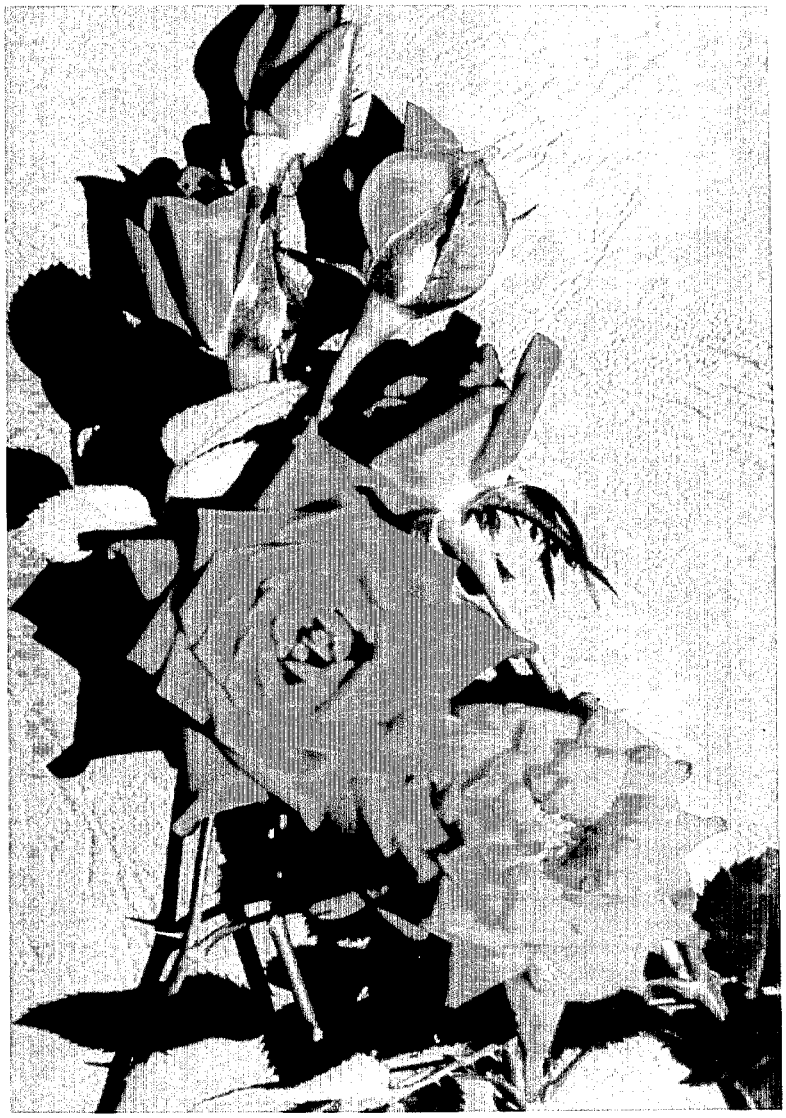

* * * * *